United States Patent
Li et al.

(10) Patent No.: US 10,865,432 B2
(45) Date of Patent: Dec. 15, 2020

(54) USING BLOOD CULTURE PLATFORMS FOR COMMERCIAL STERILITY TESTS

(71) Applicants: Becton Dickinson Holdings Pte LTD., Singapore (SG); Xiao Li, Germantown, MD (US); Yan Zhang, Suzhou (CN); Jianwei Liu, Suzhou (CN)

(72) Inventors: Xiao Li, Germantown, MD (US); Yan Zhang, Suzhou (CN); Jianwei Liu, Suzhou (CN)

(73) Assignee: BECTON DICKINSON HOLDINGS PTE LTD., Singapore (SG)

( * ) Notice: Subject to any disclaimer, the term of this patent is extended or adjusted under 35 U.S.C. 154(b) by 205 days.

(21) Appl. No.: 15/313,683

(22) PCT Filed: May 26, 2015

(86) PCT No.: PCT/US2015/032445
§ 371 (c)(1),
(2) Date: Nov. 23, 2016

(87) PCT Pub. No.: WO2015/183816
PCT Pub. Date: Dec. 3, 2015

(65) Prior Publication Data
US 2017/0191110 A1 Jul. 6, 2017

(30) Foreign Application Priority Data

May 27, 2014 (CN) .......................... 2014 1 0227620

(51) Int. Cl.
*G01N 33/00* (2006.01)
*C12M 3/00* (2006.01)
(Continued)

(52) U.S. Cl.
CPC ............. *C12Q 1/04* (2013.01); *G01N 33/004* (2013.01); *G01N 33/0036* (2013.01); *G01N 33/02* (2013.01); *G01N 33/04* (2013.01)

(58) Field of Classification Search
CPC .............................. C12M 41/12; C12M 41/14
See application file for complete search history.

(56) References Cited

U.S. PATENT DOCUMENTS

| 4,945,060 A | 7/1990 | Turner et al. |
| 5,094,955 A | 3/1992 | Calandra et al. |

(Continued)

FOREIGN PATENT DOCUMENTS

| CN | 1469758 A | 1/2004 |
| CN | 1584579 A | 2/2005 |

(Continued)

OTHER PUBLICATIONS

European Search Report received in 15799085.4 dated Nov. 9, 2017, pp. 7.

(Continued)

*Primary Examiner* — Nathan A Bowers
(74) *Attorney, Agent, or Firm* — Botos Churchill IP Law LLP

(57) ABSTRACT

A system that indicates the presence or absence of microorganisms in fluid food products. The system has a bottle for receiving sample to be tested. The bottle has a sensor that will monitor and detect changes in at least one sample parameter, but no additives that contain nutrients that support microbial growth. The bottle is placed in an incubator and the sensor in the bottle is monitored for changes. The incubator is programed so that, if the sensor detects that the value of the monitored parameter has reached a certain value, then the sample is determined to be positive for microbial growth.

4 Claims, 5 Drawing Sheets

(51) Int. Cl.
*C12Q 1/04* (2006.01)
*G01N 33/02* (2006.01)
*G01N 33/04* (2006.01)

(56) References Cited

U.S. PATENT DOCUMENTS

| | | | |
|---|---|---|---|
| 5,976,892 A * | 11/1999 | Bisconte | C12Q 1/06 422/548 |
| 5,998,517 A | 12/1999 | Gentle, Jr. et al. | |
| 6,709,857 B2 | 3/2004 | Bachur, Jr. | |
| 8,262,991 B2 | 9/2012 | Carlsen et al. | |
| 2002/0031796 A1 | 3/2002 | Townsend et al. | |
| 2004/0018585 A1 | 1/2004 | Crouteau et al. | |
| 2004/0086956 A1 * | 5/2004 | Bachur, Jr. | G01N 21/171 435/34 |
| 2004/0137486 A1 | 7/2004 | Benson | |
| 2007/0269853 A1 | 11/2007 | Galiano | |
| 2007/0298487 A1 * | 12/2007 | Bachur | B01L 3/545 435/287.2 |
| 2012/0135455 A1 | 5/2012 | Nerín De La Puerta et al. | |
| 2013/0236883 A1 | 9/2013 | Atrache et al. | |
| 2014/0120605 A1 | 5/2014 | Wolters et al. | |
| 2016/0152940 A1 * | 6/2016 | Colin | G01N 21/6428 435/34 |

FOREIGN PATENT DOCUMENTS

| | | |
|---|---|---|
| CN | 101048513 A | 8/2005 |
| CN | 102439166 A | 5/2012 |
| CN | 103154262 A | 6/2013 |
| CN | 103487559 A | 1/2014 |
| CN | 203595703 U | 5/2014 |
| EP | 0301699 A2 | 6/1987 |
| GB | 2293241 A | 3/1996 |
| JP | S52102491 A | 8/1977 |
| JP | 07008294 A | 1/1995 |
| JP | 2003130827 A | 5/2004 |
| JP | 2013537406 A | 10/2013 |
| WO | 2002030478 A2 | 4/2002 |
| WO | 2010128178 A1 | 11/2010 |
| WO | 2013165615 A2 | 11/2013 |

OTHER PUBLICATIONS

Chinese First Office Action issued in corresponding CN application No. 2014102276209 dated Jul. 19, 2018.
Zheng, et al., "Study on rapid detect commercial sterilization of fungus (i.e. mushroom) cans with BacT/Alert 3D system," Food Science and Technology, No. 9, pp. 196-199 (2007).
Zheng, et al., "Application of BacT/Alert 3D System in detection of Commercial Sterilization of Konjac Cans," Food Science, vol. 29, No. 10, pp. 463-467 (2008).
Dong, et al. Heilongjiang Province CDC, Chinese Primary Health Care, vol. 23, No. 12 (Dec. 2009).
BD Bactectm FX40 Instrument User's Manual; Document No. 8090414; Catalog No. 441980.
International Search Report for PCT/US2015/032445 dated Jul. 21, 2015.
Huang Junqin, New Sensor Principle, published May 31, 1991, relevant pp. 320-324 (relevant to claims 1-14).
Chinese Office Action and Search Report issued in corresponding CN application No. 201580040012X dated Sep. 14, 2018, pp. 19.
Japanese Office Action issued in corresponding JP application No. 2016-569761 dated Mar. 12, 2019, pp. 5.

* cited by examiner

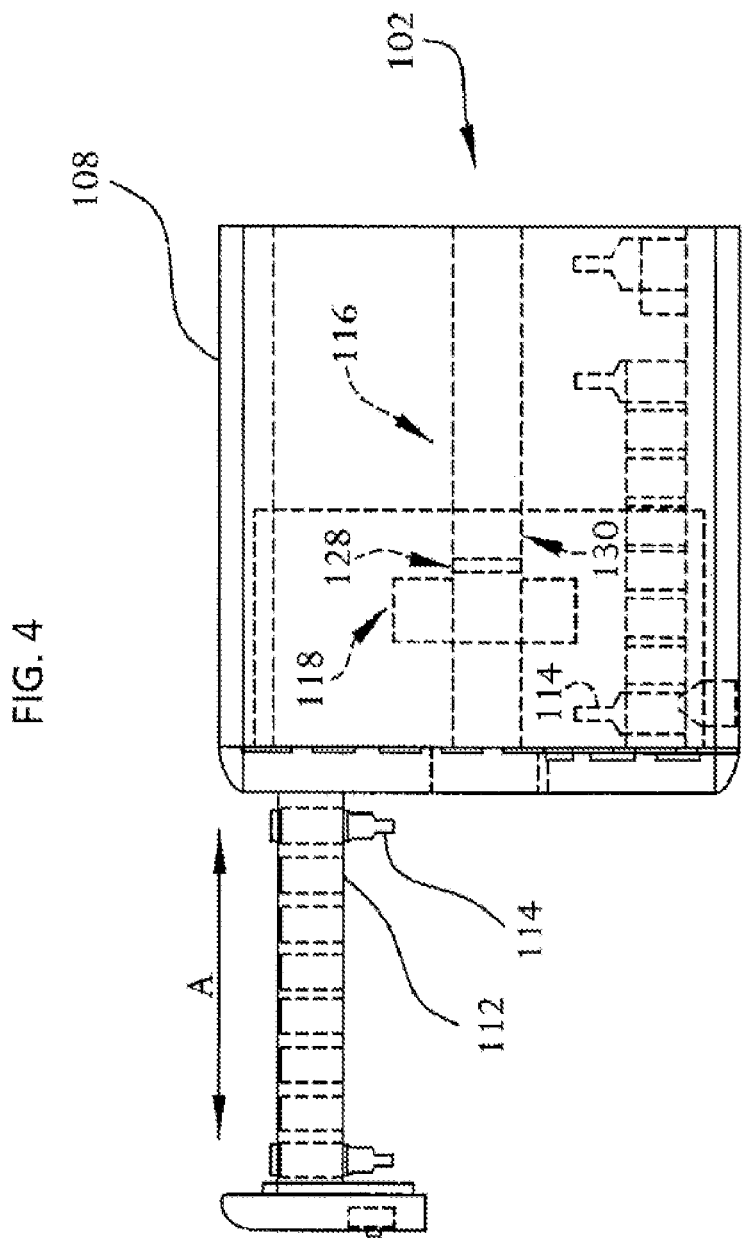

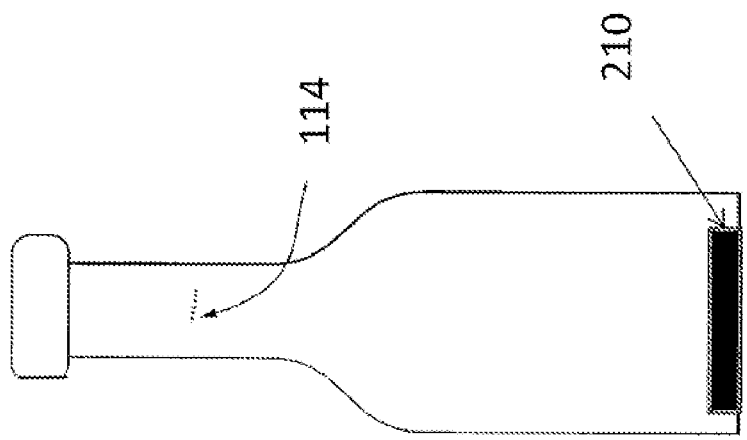

USING BLOOD CULTURE PLATFORMS FOR COMMERCIAL STERILITY TESTS

CROSS-REFERENCE TO RELATED APPLICATION

The present application is a national phase entry under 35 U.S.C. § 371 of International Application No. PCT/US2015/032445 filed May 26, 2015, published in English, which claims priority from Chinese Patent Application No. 201410227620.9, filed May 27, 2014, all of which are incorporated herein by reference.

BACKGROUND OF THE INVENTION

Food borne illnesses are a matter of public concern. Most developed nations have policies and procedures in place to ensure a reliably safe food supply, free of contamination by pathogens that can cause food borne illness.

Many countries have developed tests and protocols for inspecting food for contamination to ensure that contaminated food does not enter the food supply. One example of such a protocol is the National Food Safety Standard of the People's Republic of China. In the United States tests and standards for monitoring the food supply for pathogens are promulgated and enforced by the United States Department of Agriculture.

The goal of these tests is to keep unsafe or potentially unsafe food from consumers. However, as with any such test, the integrity of the test is crucial to identify foods that are potentially unsafe for consumption and to keep those from consumers without having samples test falsely for pathogens or contamination. False positives are an economic burden to society, both suppliers and consumers alike. So any method, system or device that inspects food must be accurate in its identification of foods that present a real public health risk.

The protocol for the Chinese inspection standard is illustrated in FIG. 1. Basically, sample 100 (such as, for example, milk) while still in the container in which it is packaged, is examined (120) for signs of container damage or a breach in container integrity. If the container is determined to be sound, the container is placed in an incubator at step 140. The container is stored in the incubator at a temperature of about 35° C. for 10 days. After that time, the container is inspected visually for any signs of bloating or expansion that are indicative of the presence of pathogens. If the container bears signatures of microbial growth in the container during incubation, the container is cooled in a refrigerator before the sample is opened and inspected. This ensures that the contaminated sample will not aspirate out of the container when it is opened. Control samples are also placed in the refrigerator as a control for the incubated samples. When the pH of the contents of the incubated samples is measured, it is compared with the pH of the contents of the refrigerated samples. A pH difference of 0.5 or more is an indication of microbial growth in the incubated sample.

Upon incubation (and cooling when appropriate) containers that exhibit physical signs of microbial growth are opened (150). An aliquot of the contents is removed (160) and placed in a sterile container. The reserved sample is inoculated onto culture media and the sample is cultured to identify the microbes that are the source of the microbial contamination.

When the container is opened, the pH of the contents is measured and the organoleptic properties of the sample (e.g. the properties experienced by the senses such as smell, color, etc.) are inspected (170). The sample is then prepared for microscopic examination (180). The microscopic examination is intended to identify the source of the microbial contamination and to determine if the microbes are pathogenic. After inspection a report is issued. The report indicates that the sample is either acceptable (i.e. commercial sterilization) or not acceptable (non-commercial sterilization).

The methods described in FIG. 1 are time consuming due to the long waits for incubation of the sample. Attempts have been made to accelerate the inspection of such samples using an automated system for detecting microbial growth in samples. Zheng, J., et al., "Study on rapid detect commercial sterilization of fungus (i.e. mushroom) cans with BacT/ALERT 3D system," Food Science and Technology, No. 9, pp. 196-199 (2007) report three days to detection using the BacT/ALERT 3D system. In BacT/Alert the sample is placed in a bottle with culture media. The bottle also has a $CO_2$ sensor. The sensor detects the presence of carbon dioxide in the sample. If the system detects an increase in the carbon dioxide content of the sample bottle beyond a certain level during incubation, the system flags the sample as positive for microbial growth. For this study, two kinds of bottles containing media were used. One (the i AST bottle) contained media for aerobic bacteria detection and the other (the i NST bottle) contained media for anaerobic bacteria detection. The bottles (which contained media) were spiked with low levels of different kinds of bacteria and 10 ml of the product (solution in mushroom cans). Time to result using BacT/Alert was listed in Table 1 and was reported as in the range of 16 hours to about 30 hours. Also reported is a non-spiked sample experiment using 45 cans containing mushrooms. The results from the BacT/Alert were compared with the results from inspection using the Chinese protocol referred to as the standard test protocol herein. BacT/Alert identified one positive sample among the 45 samples, and the contamination was verified using the standard test protocol.

Zheng, J., et al., "Application of BacT/Alert 3D System in detection of Commercial Sterilization of Konjac Cans," Food Science, Vol. 29, No. 10, pp. 463-467 (2008) describes testing Konjac Cans with BacT/Alert 3D. Samples from fifty-nine cans (not spiked) were tested. The results were compared with the results of cans tested using the standard test. Three containers of sample were used for this test. From one container, 10 ml of sample were added to each BacTAlert bottle. Specifically, 10 ml of sample was added to each of the i. AST and ii. NST bottles. The second container was analyzed by the standard test protocol and the third container was held at room temperature for follow up tests. For the cans tested using the standard test protocol, none of the cans failed quality control. However, nineteen of the samples tested with BacT/Alert were reported as positive for microbial growth in one or both bottles. These positive results were considered false positives when compared with the control (testing by the standard test). Among the nineteen BacT/Alert positive samples, three of them were confirmed not to contain microorganisms. To confirm the presence or absence of microorganisms, sample from positive bottles were inoculated on five different standard media to detect the present or absence of microbial growth. Meanwhile sample from the positive bottles was also examined under a microscope for evidence of microbial growth. From these it was determined that the three positive samples were false positive samples since, for all three of these samples, there was no sign of microbial growth from either the inoculated cultures or the samples subjected to examination by microscope. Various bacteria were isolated from the other sixteen bottles identified as positive through testing using BacT/Alert. According to this article, the Konjac cans probably contain some live microorganisms, but those microorganisms cannot grow in the Konjac cans due to the high pH environment (10-12.5). Therefore, in these cans, whatever microorganisms might be present are not pathogenic, did not render the contents unsafe for consumption, and would have passed the standard testing protocol established by the Chinese government. Nevertheless, once the samples were diluted in bottles containing culture media for testing in BacT/Alert, the microorganisms were able to grow and triggered the BacT/Alert instrument to report positive results.

Dong, R., et al. Heilongjiang Province CDC, Chinese Primary Health Care, Vol. 23, No. 12 (December 2009) describes the use of BacT/Alert for evaluating milk sterility. In this study, one kind of ultra-high temperature (UHT) milk was spiked with 2 bacteria strains (*E. coli* and *B. cereus*). As both bacteria strains grow in an aerobic environment, only the AST bottle was evaluated. The test demonstrated that a larger volume of sample was more sensitive, but did not address the issue of false positives as it did not compare the results obtained using BacT/Alert with the standard test protocol.

Accordingly, alternative methods and systems for testing food for pathogens that have reduced time to detection but compare favorably with standard test protocols in terms of the number of false positives or false negatives continue to be sought.

BRIEF SUMMARY OF THE INVENTION

A system for testing fluid foods for contamination. The system uses a sample container that is adapted to be used in an incubator that monitors a sample disposed in the container for evidence of microbial growth. In this regard there is a sensor disposed in the container. The sensor monitors at least one parameter of the sample as the sample is heated in the incubator. The parameter is a condition of the sample that will change should microbial growth occur in the sample during incubation. In this regard the sensor will provide a response to changes in a sample parameter that change in response to the metabolic activity of microorganisms. Such parameters include the concentration of oxygen in the sample, the concentration of carbon dioxide in the sample, or the pH of the sample.

When monitoring the sensor, the system will flag a bottle as positive for the presence of microorganisms if the measured value of the parameter exceeds a predetermined value. The sensor is placed in the container such that, when the sample is introduced into the container, the sensor is in contact with the sample. The system is programmed with the predetermined threshold value of the monitored parameter associated with microbial growth. In this regard, the measured parameter will increase if the measured parameter is produced by microorganism metabolic activity (e.g. $CO_2$). It follows that the parameter will decrease if the value measure parameter is consumed by microorganism metabolic activity (e.g. $O_2$).

The system has a receptacle in the incubator for receiving the sample containers. The sample containers are positioned such that the system detector can monitor the sensor during incubation of the sample in the incubator. The sample containers are presented for the introduction of sample therein without containing additives that include nutrients for microbial growth.

Also described is a method for testing fluid foods for microbial contamination. In this method a test sample is drawn from a commercially packaged sample under inspection. The test sample is introduced into a sterile container with a sensor that monitors a parameter associated with microbial growth. The sample is introduced into the container in liquid form. However, the sample can be a liquid sample (for example milk) or brine or liquid packaged with an otherwise solid sample, or a solid sample that has been liquefied for testing. The sample is referred to as a liquid sample herein, with the sample under test being liquid at ambient and testing temperatures. The sensor is placed in the container so that it will contact the test sample during subsequent incubation. The container has no nutrients that support microbial growth therein. The sample is then incubated at a temperature of about 30° C. to 38° C. while monitoring the sensor for changes in the parameter monitored by the sensor. If the sensor reading is a predetermined value associated with microbial growth, the sample is flagged as a sample as positive for microbial growth.

BRIEF DESCRIPTION OF THE DRAWINGS

These and other objects, advantages and novel features of the invention will be more readily appreciated from the following detailed description when read in conjunction with the accompanying drawings, in which:

FIG. 4 is a cutaway top view of the instrument in FIG. 3; and

FIG. 5 is a BACTEC bottle configured for use in the system and method described herein.

DETAILED DESCRIPTION

Figure 1:
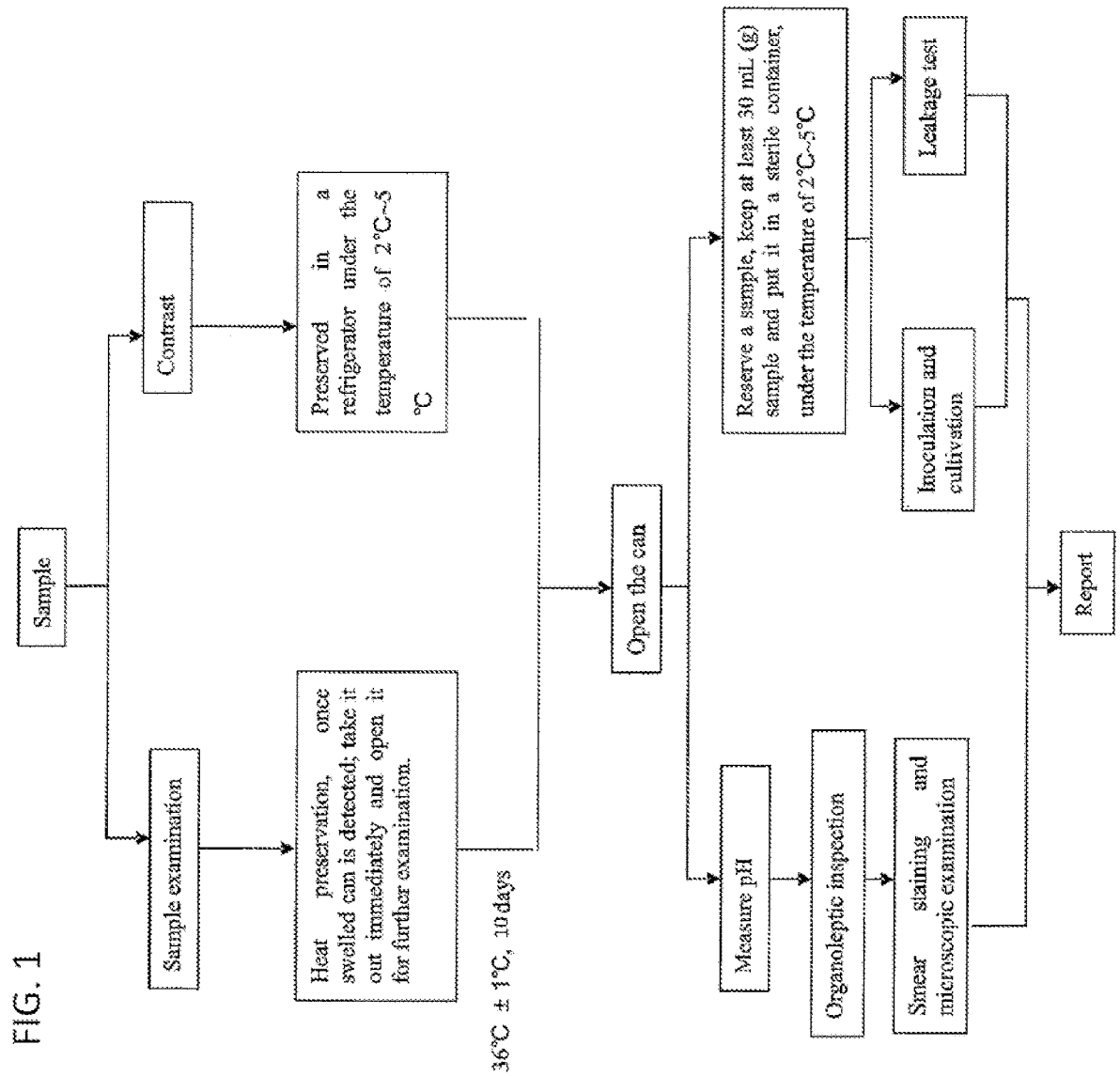
FIG. 1 is a flow diagram of the standard test protocol.
Figure 2:
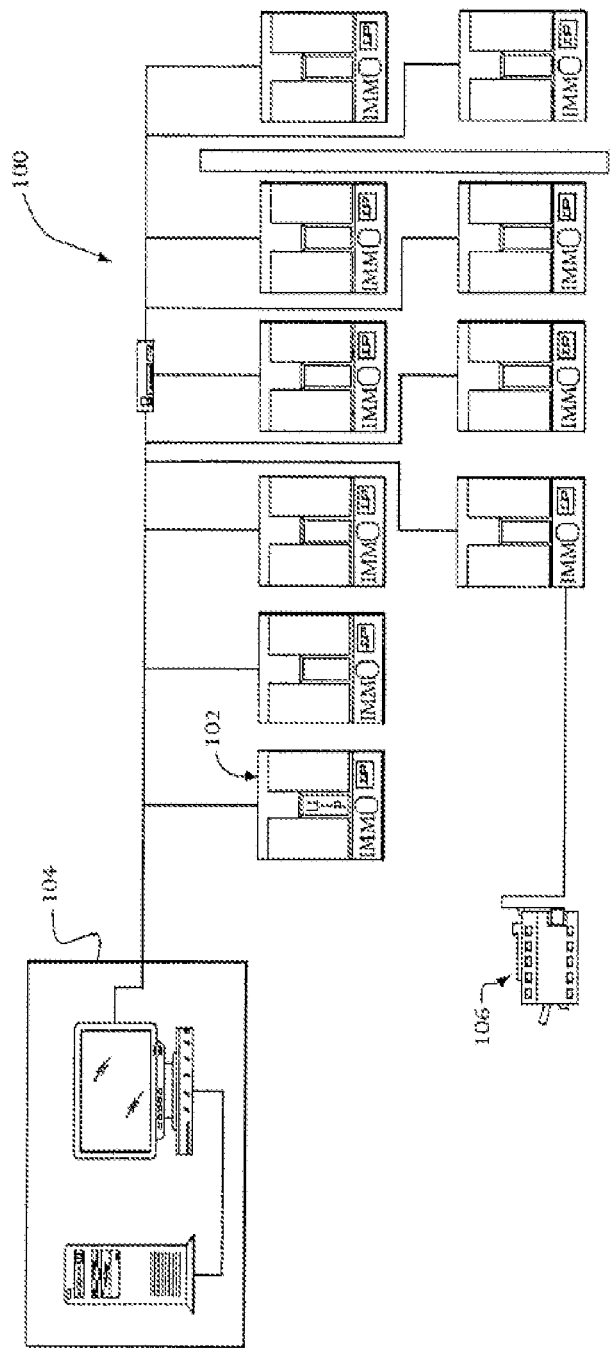
FIG. 2 is a block diagram of a system employing multiple incubation and measurement instruments according to an embodiment of the present invention, which each uses photothermal spectroscopy to monitor the concentration of a gas, such as oxygen or carbon dioxide, in sample bottles, to thus detect for microorganism growth in the sample bottles.

A system 100 for detecting growth of microorganisms in sample cultures according to an embodiment of the present invention is shown in FIG. 2. As illustrated, the system 100 includes a plurality of incubation and measurement modules 102 that are connected to a central computer 104. The central computer 104 can control the incubation temperatures and times, as well as the timing of the measurements performed by the modules 102 and can collect and classify the data readings obtained by the modules 102. The system 100 can also include a data output device, such as a printer 106 that can be controlled by the central computer 104 to print data readings obtained by the incubation and measurements modules 102.

Examples of such systems are well known to those skilled in the art and are not described in detail herein. One example of such a system is the BD BACTEC™ FX40 which is commercially obtained from Becton Dickinson. The operation of the BD BACTEC™ FX40 is described in the BD BACTEC™ FX40 Instrument User's Manual which is Document Number 8090414 and Catalog Number 441980 which is incorporated by reference herein. The operation of BD BACTEC™ FX40 and other such instruments (for example Soleris® from Neogen Corporation of Lansing Mich.) is well known to one skilled in the art and not described in detail herein.

Figure 3:
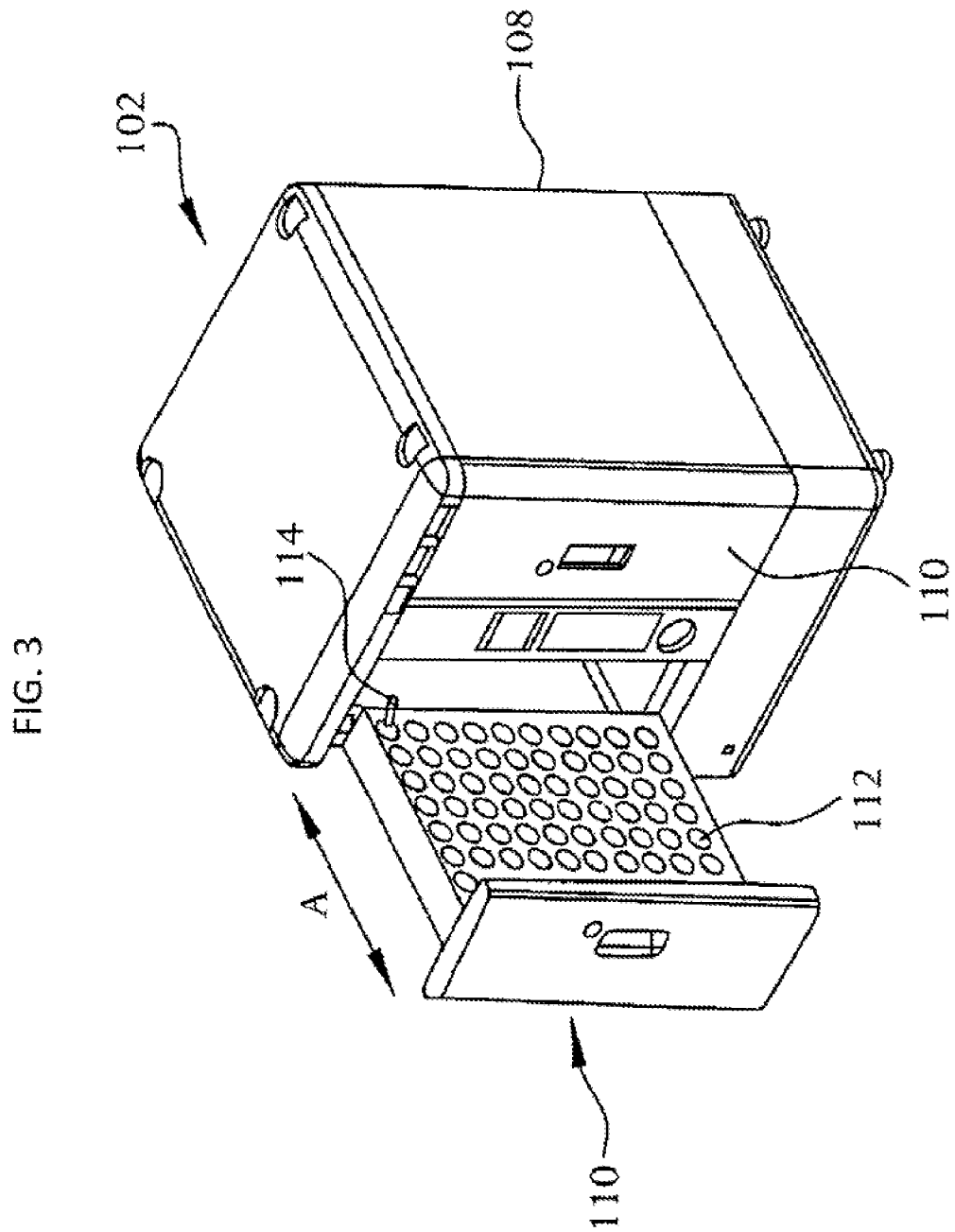
FIG. 3 is a detailed view of an instrument employed in the system shown in FIG. 1.

Further details of the incubation and measurement modules 102 are shown in FIGS. 3 and 4. As illustrated, each incubation and measurement module 102 in this example includes a housing 108 and two shelves 110 that can be slid into and out of the housing 108 in a direction along arrow A. Each shelf 110 includes a plurality of openings 112, each of which is adapted to receive a sample bottle 114. The openings 112 are arranged in a plurality of rows and columns as shown, and each shelf 110 can have any practical number of openings. For example, the openings 112 can be arranged in nine rows, with nine columns in each row, thus totaling 81 openings 112 per shelf 110.

When a sample is to be analyzed by the incubation and measurement module 102, the sample is placed in a sample bottle 114, and the sample bottle 114 is loaded into a respective opening 112 in the incubation and measurement module 102. The sample bottle 114 is a closed sample bottle in this example. The incubation and measurement module 102 can further include a keyboard, a barcode reader, or any other suitable interface that enables a technician to enter information pertaining to the sample into a database stored in a memory in the incubation and measurement module 102, in the central computer 104, or both. The information can include, for example, patient information, sample type, the row and column of the opening 112 into which the sample bottle 114 is being loaded, and so on.

Each incubation and measurement module 102 further includes a movable monitoring assembly 116 (including sensor head housing 118, vertical shaft 128 and horizontal shaft 130) which is capable of monitoring the contents of a medium in the sample bottles 114 by monitoring signals from a sensor 210 disposed inside the sample bottle 114. See FIG. 5. Such sensors monitor a parameter in the sample bottle 114 during incubation. Such samples include oxygen levels, carbon dioxide levels, pH, etc. The sensors will detect a change in such conditions over time. Such sensors are well known to one skilled in the art and not described in detail herein. The incubator is configured so that, when the value of the parameter being monitored crosses a certain threshold, the system flags the bottle (and its contents) as positive for the growth of microorganisms.

As noted above, it is important to ensure that the food supply is not contaminated by pathogens. According to the world health organization (WHO/FAO), the goal for the food supply is commercial sterility. This is defined as 'the absence of microorganisms capable of growing in food at normal non-refrigerated conditions at which the food is likely to be held during manufacture, distribution and storage'.

The standard test protocol for commercial sterility that is recommended by People's Republic of China National Standard for Food Safety (GB 4789.26-2013), is to incubate the packaged food at 36° C.+/−1° C. for 10 days, look for bloated packages, and then open all the packages for pH testing, visual and microscopic inspections.

Although the cost per manual test is relatively low, the manual protocol is a time consuming and laborious process. The requirement for large capacity incubators (to accommodate all manner of foods in bulky packaging) adds significant cost to the food manufacturers and to those organizations that test the food. In the embodiments described herein, conventional instruments for detecting microbial growth in blood cultures have been adapted and modified to monitor food for the presence or absence of microorganisms. The use of such instruments, such as BD BACTEC™ FX40, in the methods described herein provide a method and system that delivers much faster time to result while controlling the number of false positives and false negatives. Therefore, the system and methods described herein provide a much faster time to result without a significant increase in the number of false positives or false negatives achieved by prior methods.

In the method described herein, the food sample (e.g. milk) is introduced into a sample bottle configured for use in a system that monitors blood cultures for microbial growth. The sample bottle 114 has a sensor 210 disposed in the interior, preferably in a location where the sensor will be in contact with the sample when the sample is introduced into the bottle. The bottle 114 is sterile and the air is substantially completely evacuated therefrom.

The bottle volume is about 50 ml. The size of the bottle will vary, and so will bottle volume. However, bottles must be of a suitable volume to receive a sample volume that will ensure adequate sensitivity of the sample. In this regard, if the bottles can only receive a very small sample, then the sample might not be representative of the sample contents in terms of the contaminants (if any) in the sample portion. For example, if the container size is one gallon, and the sample volume for testing is only 10 ml, there is a real possibility that the sample portion may not contain a microorganism even if they were present in the container. For the method and apparatus described herein the minimum sample size would be no less than about 10 ml and preferably not less than 50 ml.

The bottle is preferably under some vacuum so that the sample can easily be drawn into the sample container. Apparatus for drawing liquid samples into containers are well known and not described in detail herein.

The sensor is typically a $CO_2$ sensor. Examples of suitable sensors are described in U.S. Pat. No. 5,998,517 to Gentle et al. which is hereby incorporated by reference. The sensor, e.g. a silicone sensor, is disposed in a gel matrix. The sensor is interrogated during incubation to monitor changes in carbon dioxide levels in the sample. When the carbon dioxide levels in the bottle exceed a predetermined threshold, the bottle is flagged as containing sample that has tested positive for the presence of microorganisms therein.

The sample bottle 114 into which the sample is dispensed does not contain any nutrient media that facilitates microbial growth. For this application it is important to preserve the sample integrity and ensure that nutrients for microbial growth come from the sample itself and not from additives to the sample. As illustrated in the following example, the number of false positive surprisingly increases when culture media is present in the container in which the sample is disposed, incubated, and monitored for the presence or absence of microbial growth.

Using UHT milk as an example of a food sample, the sample bottles that did not contain culture media were prepared. In one embodiment the bottles are those that are configured for use in the BACTEC blood culture device. The samples (50 ml) of UHT milk were obtained from three different kinds of cartons. The samples were spiked with microorganisms (*B. cereus, B. licheniform, C. perfringens, S. aureus; P. aeruginosa; L. fermentus*). For comparison, 10 ml of the same spiked UHT milk samples were also added to BACTEC bottles containing Lytic/Anaerobic media. All the BACTEC bottles were loaded in a FX200 or BACTEC 9240 for detection.

UHT milk samples spiked with the same concentrations of microorganisms were tested by the standard test protocol described above. The results using empty BACTEC bottles with 50 ml of milk samples were shown to better correlate to the results obtained when the standard test protocol was used. Although applicants do not wish to be held to a particular theory, applicant believe that the lower false negative rates for samples tested in bottles without media compared to samples in bottles with media are due to the larger sample size (50 ml vs 10 ml) and/or the selection of a media that yields a false result. A larger sample size is more sensitive to samples that have a low concentration of organisms.

It was also observed that certain bacteria (e.g. *C. perfringens*) did not grow in two kinds of milk cartons when those cartons were tested using the standard test protocol described above. When 50 ml samples were tested in bottles without media using BACTEC, the same observation was made. Thus, the method described herein yields results compatible with the established test protocol. In contrast, when 10 ml samples were introduced into bottles that contained Lytic/Anaerobic media, those samples tested positive for microorganism growth. This is interpreted as a false positive. Therefore, the rate of false positives was lower using BACTEC bottles without media that with media (using the standard test protocol).

Milk that has been pasteurized using ultra high temperatures (UHT milk) was obtained in 3 different kinds of cartons: i) Prepack (soft plastic); ii) Tetra Pack (hard plastic); and Tetra Brik (hard cardboard box). The products were purchased from local supermarkets in China.

Bacteria stock solutions were diluted to a very low concentration and the same amount was spiked into 2 identical cartons of UHT milk (0.01 cfu-0.5 cfu/ml were spiked into each carton). One of the spiked cartons was sealed and put into a 36° C. incubator (the prior art reference method, also referred to as the standard protocol), and the other one was used for studies on BACTEC bottles with and without media.

In the reference method, the cartons were examined daily for leakage/swelling, and were opened right away for further examination if abnormalities in the cartons were observed. Other cartons that appeared normal were left in the incubator for about 10 days before being opened for further tests. The tests were: i) pH; ii) smell; iii) inspection for precipitates or aggregated material; and iv) plating the material on TSA and RCM agars and looking for colony growth after incubation at 36° C. The samples were identified as contaminated samples if any of the above parameters appeared abnormal.

A portion of the samples were disposed in bottles that contained the standard Lytic/Anaerobic media for BACTEC. This media is commercially obtained from Becton Dickinson and is not described in detail herein.

For another set of bottles, the media was aspirated out of bottles, as was any residual air. In those bottles, 50 ml of spiked UHT milk was injected.

For a third set of bottles, 5 ml saline was added to empty BACTEC bottles which were then autoclaved. Air in those bottles was aspirated out by a syringe to generate sufficient vacuum in the bottle to draw in the sample. Then ml spiked milk was injected into the bottles, and 2 duplicate bottles were used for each experiment. The bottles were loaded into a BACTEC FX 200 or a BACTEC 9240 for detection. Samples were considered commercially sterile if the samples were still negative after five days of incubation.

The same spiked sample carton was the source of sample for studies in bottles without media and for the studies in bottles with media. Each carton contained more than 200 ml milk and therefore there was an adequate amount of sample for both studies. The amount of spiked sample injected in each bottle containing Lytic/Anaerobic media was 10 ml. Two duplicate bottles were used for each experiment. For the sample spiked with *P. aeruginosa*, one bottle containing aerobic media was used in addition to two bottles with anaerobic media therein. Samples were considered commercially sterile if the samples were still negative after 5 days of incubation.

TABLE 1

Media Effect on Result for Samples Spiked with *P. aeruginosa*

| 35 cfu P. aeruginosa/box | Lytic/Anaerobic bottle (Cat# 442265) Without media 50 ml/sample Time to Result (h/min) | Lytic/Anaerobic bottle Cat# 442265 With media 10 ml/sample Time to Result (h/min) | Standard Aerobic bottle Cat# 442260 With media 10 ml/sample Time to Result (h/min) | 36° C. Incubation (standard method) |
|---|---|---|---|---|
| Tetra Brik 250 ml/box | 13:15 (Bottle 1) 13:15 (Bottle 2) | Negative (Bottle 1) Negative (Bottle 2) | 16:13 | 8 days, no swelling, milk spoiled |
| Tetra Pack 231 ml/box | 14:54 (Bottle 1) 15:14 (Bottle 2) | Negative (Bottle 1) Negative (Bottle 2) | 16:53 | 8 days, no swelling, milk spoiled |
| Prepack 200 ml/box | 13:14 (Bottle 1) 13:24 (Bottle 2) | Negative (Bottle 1) Negative (Bottle 2) | 16:03 | 8 days, no swelling, milk spoiled |

Results demonstrated that not all organisms will grow in all media. As demonstrated above, *P. aeruginosa* grew in aerobic media but did not grow in an aerobic media. Obviously, if bottles without media are used, one does not have to select a specific media in which the organism will grow. If bottles without media are used, there is no concern with media selection. The test results from samples in bottles without media were completely consistent with the results for samples in media in which the target organism grew (the aerobic media). The results for samples disposed in bottles without media had complete correspondence for the result for samples incubated using the standard protocol.

TABLE 2

Effect of Sample Size on Results with Samples Spiked with *L. fermentum*

| | Saline bottle Without media 50 ml/sample Time to Result (h/min) | Lytic/Anaerobic bottle Cat# 442265 With media 10 ml/sample Time to Result (h/min) | 36° C. Incubation |
|---|---|---|---|
| Tetra Brik 250 ml/box 45 cfu/box | 23:35 (Bottle 1) 23:05 (Bottle 2) | 23:04 (Bottle 1) Negative (Bottle 2) | 8 days, slightly swelling, no change in milk appearance, pH decreased > 0.5 |
| Tetra Pack 231 ml/box 20 cfu/box | 1 day, 05:03 (Bottle 1) 19:03 (Bottle 2) | 21:03 (Bottle 1) Negative (Bottle 2) | 8 days, no swelling, no change in milk appearance, pH decreased to about 0.5 |
| Prepack 200 ml/box 44 cfu/box | 22:04 (Bottle 1) 24:04 (Bottle 2) | 21:03 (Bottle 1) Negative (Bottle 2) | 8 days, no swelling, some precipitates in milk, pH decreased > 0.5 |

This experiment showed that false negatives were obtained in the bottles with media and only ten milliliters (mls) of sample. The false negatives were not consistently obtained, so at least two bottles would be required for bottles that contain only ten mls of sample combined with media. The two bottles are necessary to flag false positive or false negatives. Such false positives or false negatives would be flagged by inconsistent results for otherwise identical samples. False negatives did not result when the sample size was 50 mls. The no-media test results matched the reference method (both showed contamination), while half of the bottles using media (with 10 ml sample size) generated false negative results.

TABLE 3

Effect of media on growth of organisms that could not grow in the sample without the media for samples spiked with spiked with *C. perfringens*

| |